US006760105B2

(12) United States Patent
Oshida et al.

(10) Patent No.: US 6,760,105 B2
(45) Date of Patent: Jul. 6, 2004

(54) METHOD AND APPARATUS FOR INSPECTING DNA AND METHOD FOR DETECTING FLUORESCENCE

(75) Inventors: Yoshitada Oshida, Chigasaki (JP); Satoshi Takahashi, Hitachinaka (JP); Taisaku Seino, Tsuchiura (JP); Kenji Yasuda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 339 days.

(21) Appl. No.: 10/053,976

(22) Filed: Jan. 18, 2002

(65) Prior Publication Data
US 2002/0140933 A1 Oct. 3, 2002

(30) Foreign Application Priority Data

Mar. 30, 2001 (JP) ........................................ 2001-097966

(51) Int. Cl.[7] .............................................. G01N 21/64
(52) U.S. Cl. ...................... 356/317; 356/417; 356/318; 250/458.1; 250/459.1; 422/82.05
(58) Field of Search ................................ 356/317, 318, 356/417; 250/458.1, 459.1; 422/82.05, 82.07, 82.08, 63; 436/172

(56) References Cited

U.S. PATENT DOCUMENTS

| 5,528,045 | A | * | 6/1996 | Hoffman et al. | ......... 250/458.1 |
| 6,078,390 | A | | 6/2000 | Bengtsson | |
| 6,310,687 | B1 | * | 10/2001 | Stumbo et al. | ............. 356/317 |
| 6,471,916 | B1 | * | 10/2002 | Noblett | .................... 422/82.08 |
| 6,646,271 | B2 | * | 11/2003 | Yokokawa et al. | ...... 250/458.1 |
| 6,650,411 | B2 | * | 11/2003 | Odoy et al. | ................. 356/318 |

FOREIGN PATENT DOCUMENTS

JP 09-105738 4/1997

* cited by examiner

Primary Examiner—Richard A. Rosenberger
Assistant Examiner—Layla Lauchman
(74) Attorney, Agent, or Firm—Townsend and Townsend and Crew LLP

(57) ABSTRACT

A DNA sample added with a plurality of fluorescent marks is irradiated with excitation lights having a plurality of wavelengths and when fluorescence intensities are detected separately, the excitation light and a position on the sample are relatively changed over a desired area once to thereby detect the plurality of fluorescent marks at high speed.

17 Claims, 13 Drawing Sheets

FIG. 3
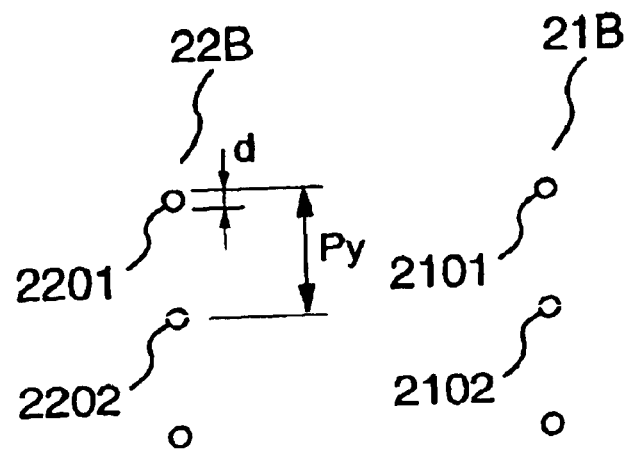
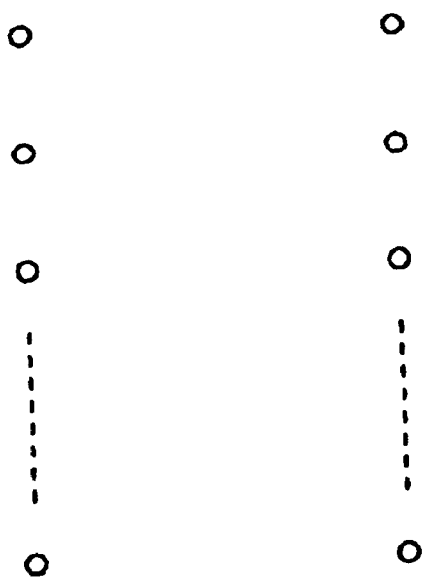
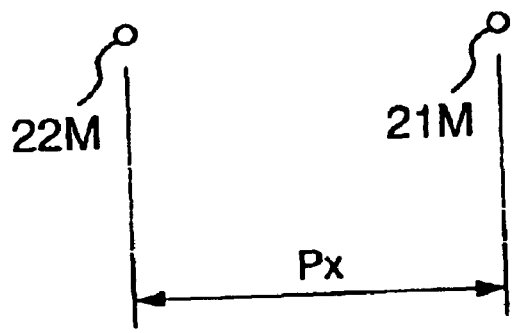

METHOD AND APPARATUS FOR INSPECTING DNA AND METHOD FOR DETECTING FLUORESCENCE

BACKGROUND OF THE INVENTION

The present invention relates to a method and an apparatus for irradiating DNA marked with fluorescence or a fluorescent material with excitation light to inspect the DNA and a fluorescence detection method and more particularly to a method and an apparatus for detecting and inspecting DNA marked with a plurality of kinds of fluorescence samples or a plurality of kinds of fluorescent materials at high speed.

As a method for irradiating fluorescence-marked DNA with excitation light to inspect the DNA, there is a method for focusing laser light constituting excitation light on a sample as a single spot beam to detect fluorescence and collecting a fluorescence image by means of scanning of the excitation light and the sample. In detection of a plurality of fluorescent marks, a desired all area of a sample is first scanned with first excitation light to obtain a fluorescent image of a first fluorescent mark and the desired all area of the sample is then scanned with second excitation light again to collect the fluorescent image of a second fluorescent mark.

SUMMARY OF THE INVENTION

It is an object of the present invention to provide a high-speed detectable DNA inspection method and apparatus.

In the conventional method, a desired area is scanned with excitation light having different wavelength in accordance with a plurality of fluorescent marks and this scanning is repeated by the number of marks. In order to change a relative position of a single spot beam and a sample to inspect a desired area at high speed, it is necessary to move a stage on which the sample is placed at high speed. However, when the stage is moved at high speed, a considerable time is required for acceleration and deceleration for driving the stage since reciprocating motion is needed.

Further, when the scanning using the stage is repeatedly made for each wavelength of the excitation light, a positional shift or deviation occurs in a combined image of fluorescent images obtained by means of excitation lights when a driving accuracy of the stage and a reproduction accuracy are not sufficient. Consequently, high-speed and high-accuracy inspection of DNA required increasingly in future cannot be attained.

In order to solve the above problems, the present invention comprises measures described below.

A sample having a DNA piece added with a plurality of L kinds of fluorescence-marked materials combined to corresponding DNA is irradiated with a plurality of M kinds of minute spot excitation lights in accordance with the fluorescence-marked materials. Fluorescence intensities obtained in accordance with the fluorescence-marked materials are separately detected by means of the plurality of M kinds of minute spot excitation lights. The separately detecting operation of the plurality of fluorescent marks is made by changing a position on the sample irradiated with the spot excitation lights over a desired area by the number of times smaller than the number L of kinds of the fluorescence-marked materials, more preferably once, in order to detect the fluorescence intensities, to thereby inspect the DNA added with the plurality of kinds of fluorescence-marked materials.

Further, when the plurality of kinds of minute spot excitation lights are a plurality of minute multi-spot excitation lights, respectively, a plurality of points about the fluorescent marks can be detected at the same time to attain high-speed detection.

When different positions on the sample from one another are irradiated with the plurality of kinds of multi-spot excitation lights, fluorescence components from the fluorescent marks excited by the plurality of kinds of excitation lights can be separately detected with high accuracy without causing fluorescence components to impede one another as noise.

Irradiation with the plurality of kinds of multi-spot excitation lights is made at the same time and fluorescence obtained by the plurality of kinds of minute spot excitation lights in accordance with the fluorescence-marked materials is detected by a plurality of weak-light detection elements in accordance with respective excitation lights. The fluorescence intensities obtained in accordance with the fluorescence-marked materials are detected separately. Thus, in the photon-counting method used particularly when weak fluorescence is detected, the photon-counting can be made at the same time with respect to respective fluorescence components to make inspection at high speed in wide dynamic range.

Irradiation with the plurality of kinds of minute spot excitation lights is made in time series manner in accordance with wavelengths of the excitation lights and fluorescence obtained by the plurality of kinds of minute spot excitation lights in accordance with the fluorescence-marked materials is detected by a common weak-light detection element to respective excitation lights. The fluorescence intensities obtained in accordance with the fluorescence-marked materials are detected separately. Thus, in detection using the multi-spot, particularly, the weak-light detection element and its peripheral circuit become inexpensive.

Substantially the same position is irradiated with the plurality of kinds of minute spot excitation lights. Thus, detection by means of respective excitation lights can be made at the same place and detection with high accuracy can be made without any shift or deviation due to yawing and rolling of a stage in a combined image.

The plurality of kinds of minute spot excitation lights are turned on and off in different time zone within a time that a relative position of the spot excitation lights and the sample to be irradiated is changed by substantially one pixel. Thus, the respective fluorescent marks can be detected with high accuracy without mixing noise one another.

The plurality of kinds of minute spot excitation lights are changed stepwise at respective excitation light intensity levels within a time that a relative position of the spot excitation light and the sample to be irradiated is changed by substantially one pixel to detect the fluorescence intensity at each step, so that detection is made over a wide dynamic range at a high speed.

The DNA inspection apparatus according to the present invention is configured as follows. That is, the DNA inspection apparatus comprises one to a plurality of light sources for emitting lights having wavelengths different from one another, a plurality-of-wavelength excitation optical system for irradiating a DNA sample added with a plurality of fluorescence-marked materials with lights having the plurality of wavelengths from the light sources as minute spot excitation lights, a wavelength separation fluorescence detection system for separately detecting fluorescence intensities obtained by the respective excitation lights in accordance with the fluorescence-marked materials, a driving stage for changing a relative position of the minute spot excitation lights and the DNA sample over a desired area, and a processing unit for driving the driving stage so that the relative position of the minute spot excitation lights and the DNA sample is changed over the desired area by the number of times smaller than the number of kinds of the fluorescence-marked materials so as to construct image information of the plurality of fluorescence-marked DNAs on the sample from fluorescence detection information obtained by the detection system and the stage position information obtained by scanning by the number of times smaller than the number of kinds of the fluorescence-marked materials over the desired area.

Further, the present invention is applied to not only inspection of the fluorescence-marked DNA but also general fluorescent material emitting fluorescence peculiar to molecules such as protein.

According to the present invention, DNA to be inspected including the plurality of fluorescent marks or the samples containing the plurality of kinds of fluorescence materials cab be detected by scanning within a desired detection spread by the number of times smaller than the number of kinds of the samples containing the fluorescence materials or fluorescent marks, more preferably once, to thereby make it possible to attain detection extraordinarily fast as compared with the prior art. Consequently, a large number of objects to be inspected can be detected and inspected at high speed to attain largely temporal and economical effects.

BRIEF DESCRIPTION OF THE DRAWINGS

FIG. 3 is an enlarged plan view of multi-spot excitation light according to the present invention;

DESCRIPTION OF THE EMBODIMENTS

Figure 1:
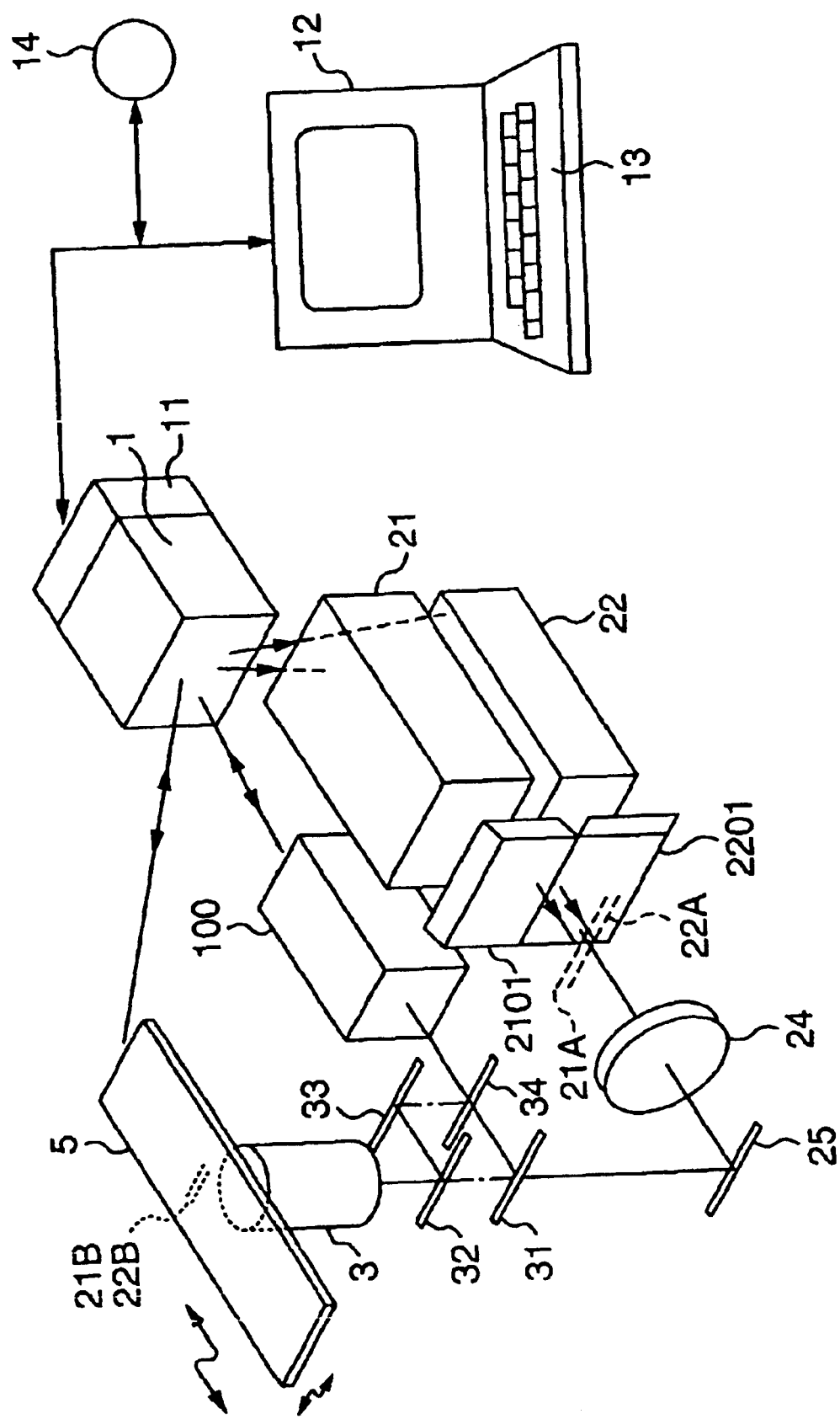
FIG. 1 is a perspective view illustrating the whole structure of a DNA inspection apparatus according to the present invention.
Figure 2:
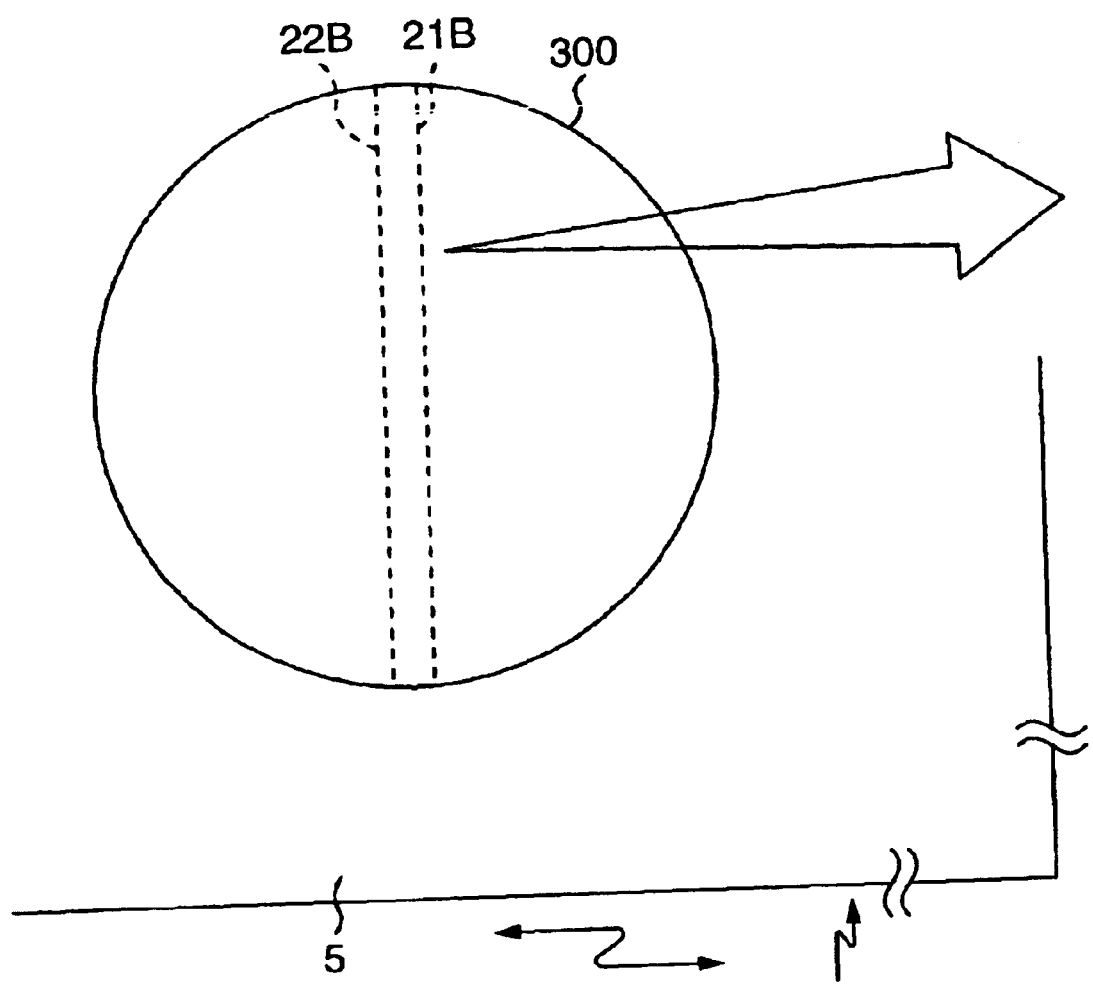
FIG. 2 is a plan view showing multi-spot excitation light within a detection field of vision according to the present invention.

FIG. 1 illustrates an embodiment according to the present invention. Numeral 1 denotes a control unit and numeral 5 denotes a sample board on which a sample including fluorescent marks or fluorescence substance is placed. Numerals 21 and 22 denotes an excitation light source and a plurality-of-wavelength excitation optical system for irradiating the sample with minute spots of excitation light, respectively, described later with reference to FIG. 9. That is, the excitation light source 21 constitutes part of a light source composed of a plurality of semiconductor lasers having a wavelength of, for example, 635 nm and an excitation optical system for irradiating the sample with minute multiple spots of light emitted from the light source. The plurality-of-wavelength excitation system 22 constitutes part of a light source formed of a YAG laser having a wavelength of 532 nm and an excitation optical system for irradiating the sample with minute multiple spots of laser light emitted from the light source. The number of minute multiple spots is 64, 32, 16 or 8 and the number of minute multiple spots is selected therefrom in accordance with a specification of an inspection system. 64 laser beams having the wavelengths of 635 nm and 532 nm emitted from the excitation light source 21 and the plurality-of-wavelength excitation system 22, respectively, form 64 multi-spot spatial images having the respective wavelengths on positions 21A and 22A by means of beam alignment units 2101 and 2201, respectively. The multiple spot spatial images are focused on the sample put on the sample board 5 as multi-spot excitation images indicated by 21B and 22B as shown in FIG. 2 by means of a tubular lens or a focusing lens 24 and an objective lens 3.

More particularly, as shown in FIG. 3, the M (64) spots each having a diameter d are arranged at a pitch Py on the sample. Numeral 21B represents the multi-spot having the wavelength of 635 nm and numeral 22B represents the multi-spot having the wavelength of 532 nm. The spaces Px between the spots 21B and 22B are not equal to one another and are several tens to several hundreds micrometers in the embodiment. The spaces can be made equal to one another depending on a specification to be targeted as described later.

Figure 4:
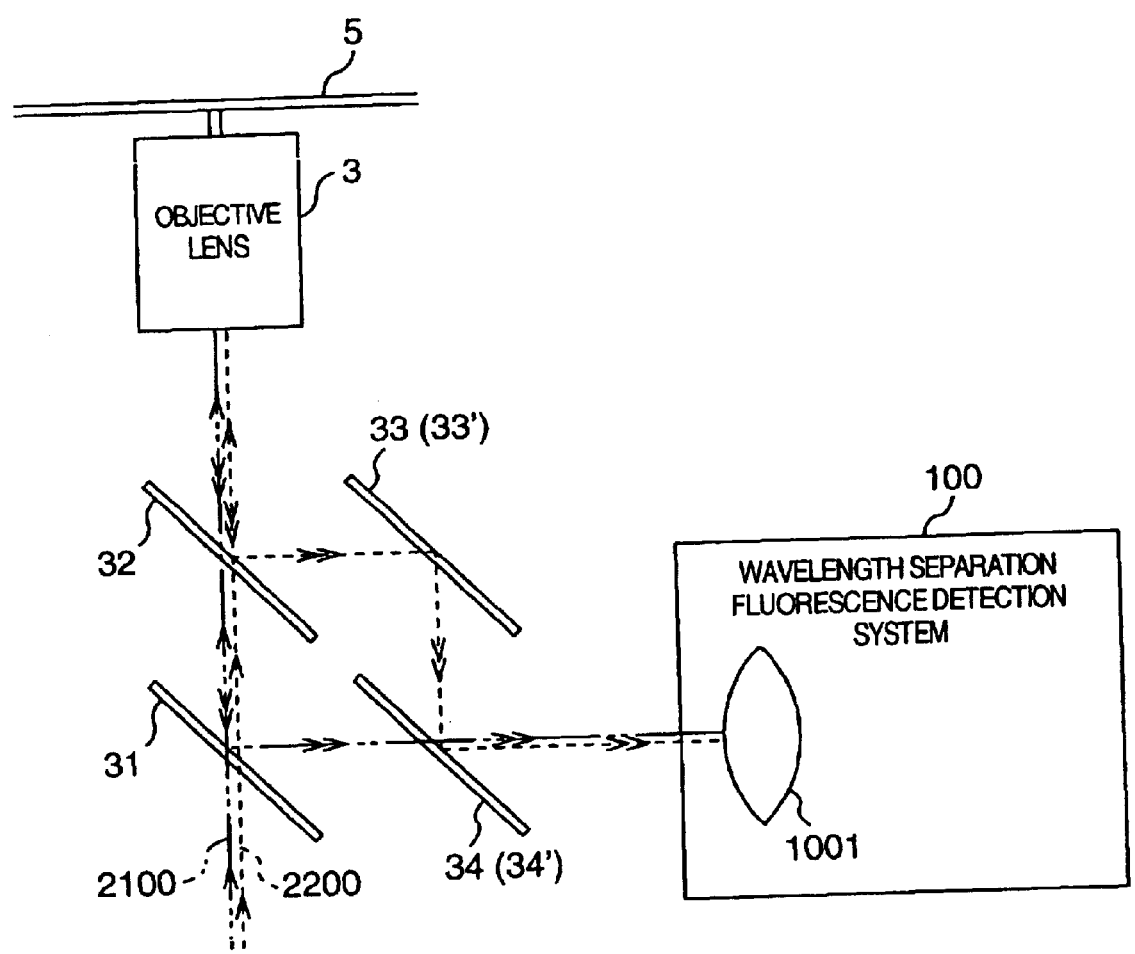
FIG. 4 is a front view showing part of an optical system in which paths of excitation light and fluorescence according to the present invention are shown.

Numerals 31 and 32 of FIG. 1 denote wavelength selection beam splitters which transmit light beams having wavelengths of 635 and 532 nm of the excitation light, respectively. When fluorescence material on the sample is excited by the multiple spots, the fluorescence material absorbs the excitation light having the wavelength of 635 nm ($\lambda1$) impinging on positions 2101, 2102, ..., 21M of the excited minute spots and emits fluorescence having a wavelength $\lambda1'$ slightly longer than the above wavelength when fluorescence material ML1 emitting fluorescence is present. The emitted fluorescence passes through the objective lens 3 having a large numerical aperture (NA) as shown in FIG. 4 and advances as shown by broken line with double arrows. The emitted fluorescence is then reflected by the wavelength selection beam splitter 32 and further reflected by wavelength selection beam splitters 33 and 34 having the same wavelength selection characteristic as the beam splitter 32 (or reflected by a mirror 33' having a high reflectivity and a wavelength selection beam splitter 34' which transmits fluorescence $\lambda2'$ and reflects $\lambda1'$ as described later) to enter a wavelength separation fluorescence detection system 100 described later in detail with reference to FIGS. 5 to 8. The wavelength selection beam splitters 33 and 34 having the wavelength selection characteristic reflect the fluorescence to thereby cut excitation lights λ1 and λ2 considerably.

On the other hand, positions 2201, 2202, . . . , 22M on the sample are irradiated with the multi-spot excitation light having the wavelength of 532 nm (λ2) different from the wavelength λ1. The sample absorbs the multi-spot excitation light and when fluorescence material ML2 emitting fluorescence is present, fluorescence having the wavelength λ2' slightly longer than the above wavelength is produced. The emitted fluorescence also shown in FIG. 4 passes through the objective lens 3 having the large numerical aperture (NA) and advances as shown by broken line with double arrows. The fluorescence then transmits the wavelength selection beam splitter 32 and is reflected by wavelength selection beam splitters 31. This reflected fluorescence transmits the wavelength selection beam splitter 34 (or 34') to enter the wavelength separation fluorescence detection system 100. When the fluorescence is reflected by the wavelength selection beam splitter 31 and transmits the wavelength selection beam splitter 34 or 34', the excitation lights λ1 and λ2 are cut considerably.

The relative position of the multi-spot excitation lights having a plurality of wavelengths and the sample is scanned once and a plurality of fluorescent marks or information of the fluorescence material detected by the wavelength separation detection system of FIG. 1 is stored once. When desired inspection specifications such as, for example, a coordinate range of an inspection area, information relative to an object to be inspected and output conditions are inputted by an input terminal 13 of FIG. 1, detection is made in accordance with the conditions and a desired output of detection results obtained is displayed on a display monitor 12, for example. Further, the results can be transmitted to a distant place through a line 14. Inputting of conditions of the above apparatus, control of the excitation light, the stage and detection of a photo-multiplier, processing of the result, outputting of the result and the like are controlled by the control unit 1 of FIG. 1.

Figure 5:
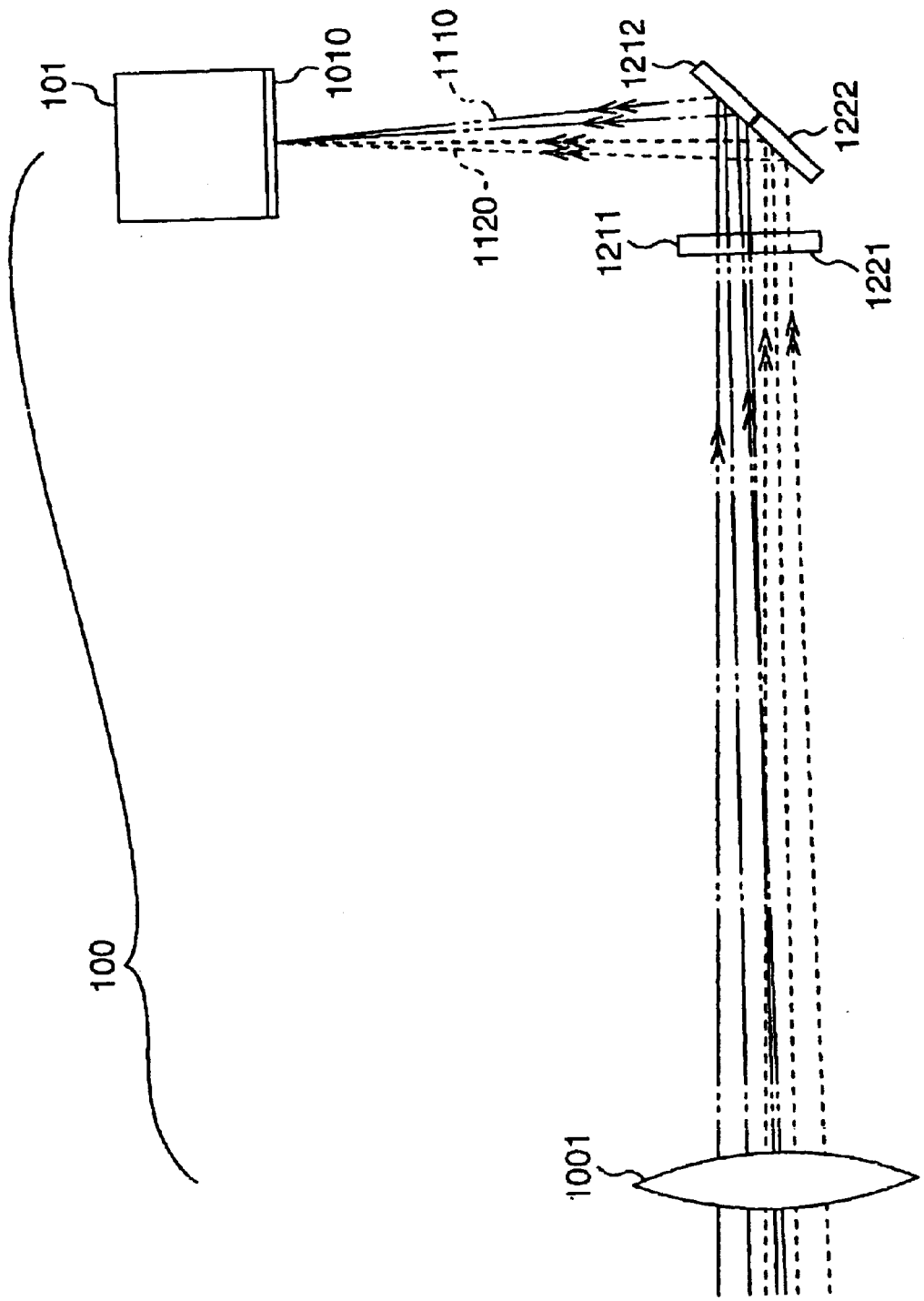
FIG. 5 is a front view showing an example of a fluorescence detection optical system according to the present invention.

FIG. 5 shows an embodiment of the wavelength separation fluorescence detection system 100. Numeral 1001 denotes a relay lens or a focusing lens. The fluorescence components emitted from different fluorescence materials ML1 and ML2 pass through the lens 1001 and are then separated into respective light fluxes at positions of interference filters 1211 and 1221. This separation is realized by shifting a position on the sample irradiated with both the excitation lights. Further, the separation is also realized by adjustment of positions or angles of the wavelength selection beam splitters 33 and 34. The separated fluorescence components λ1 and λ2 pass through the interference filters 1211 and 1221 to thereby reduce the excitation light component to an extremely small amount and remove noise in detection of fluorescence.

Figure 6:
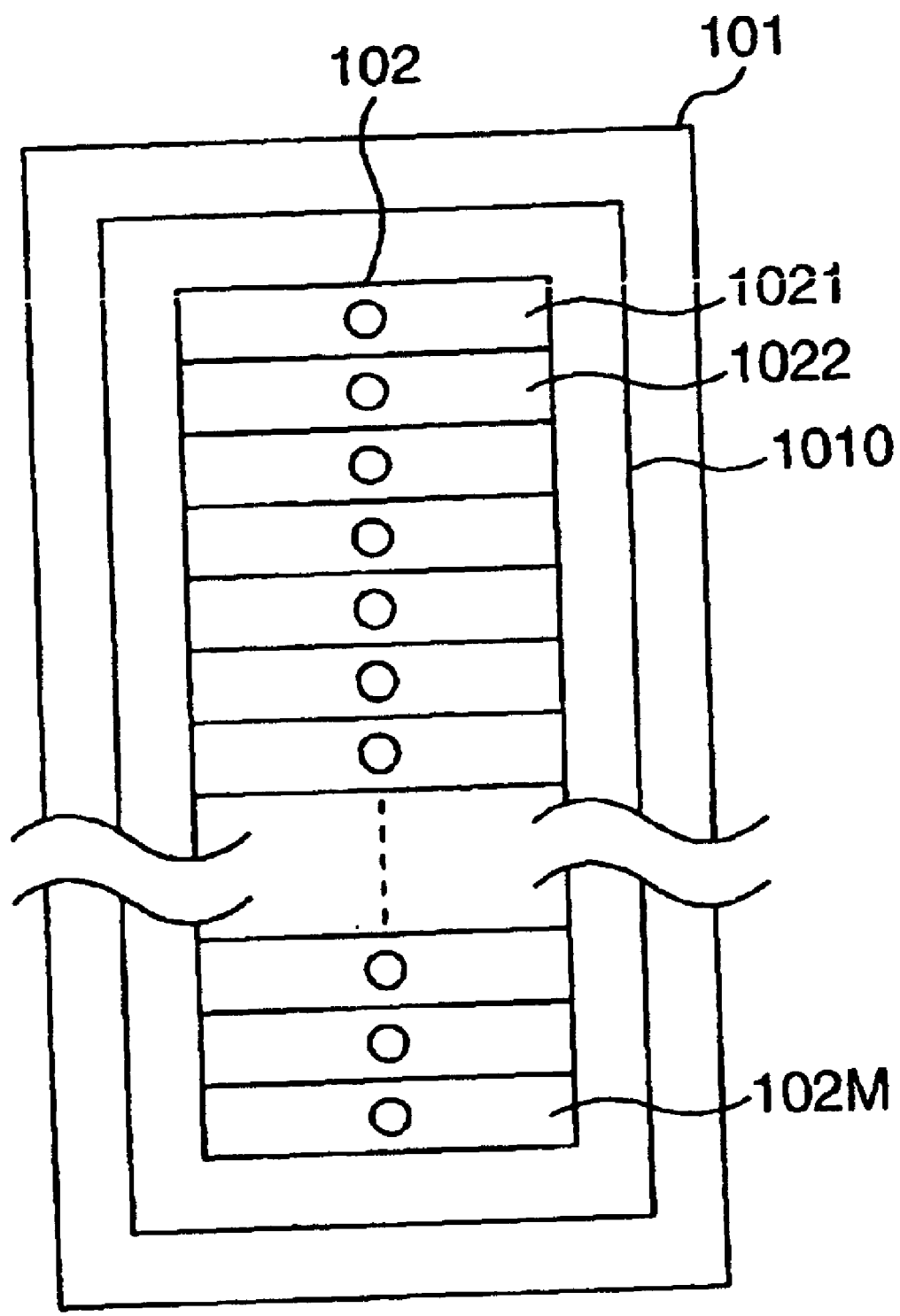
FIG. 6 is a front view illustrating a photo-multiplier showing an example of fluorescence detection spots on the photo-multiplier according to the present invention.

The fluorescence components λ1' and λ2' passing through the interference filters are reflected by wavelength selection mirrors 1212 and 1222 (or high-reflecting mirrors 1212' and 1222' of broadband) and enter a multi-channel photo-multiplier 101 shown in FIG. 6. Since the wavelength selection mirrors 1212 and 1222 transmit the excitation light component and reflect the fluorescence, the excitation light component is reduced to an extremely small amount equal to almost 0 after the reflection of the fluorescence. Since the wavelength selection mirrors 1212 and 1222 have respective reflecting planes which are not formed on one plane as shown in FIG. 5 and are inclined at an angle, both the fluorescence components reflected by the wavelength selection mirrors are focused on pinholes of a pinhole array or slits formed in a line at the front of the multi-channel photo-multiplier 101 as shown in FIG. 6.

Figure 7:
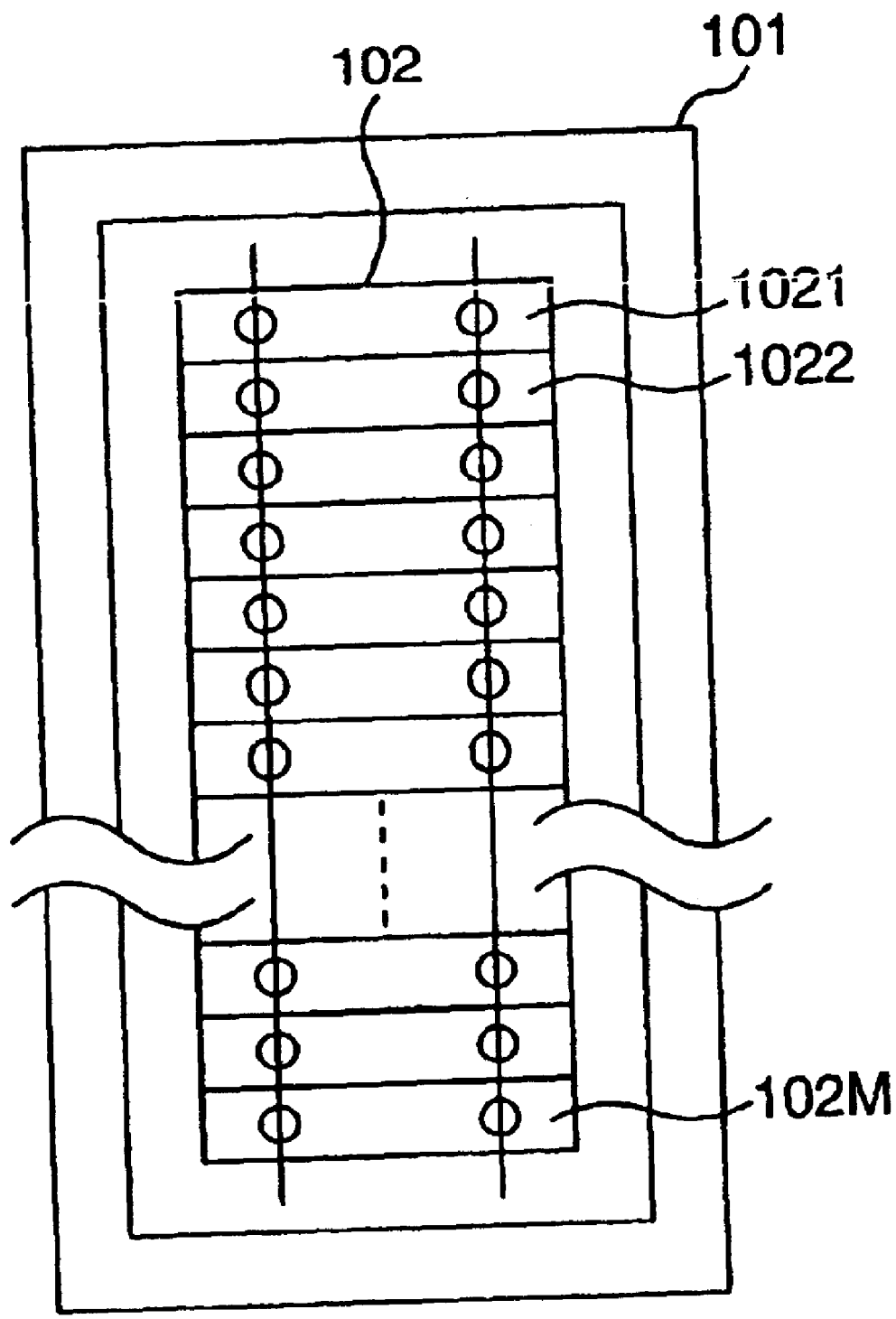
FIG. 7 is a front view illustrating a photo-multiplier showing another example of fluorescence detection spots on the photo-multiplier according to the present invention.

FIG. 7 shows an embodiment showing a detection method effective for the case where the multi-channel photo-multiplier 101 is long in a direction perpendicular to the array direction. In this case, the mirror plane of the wavelength selection mirrors 1212 and 1222 of FIG. 5 is disposed on one plane. Further, when the excitation light can be cut sufficiently until this mirror is reached, a single usual mirror may be used.

In the embodiment, since a plurality of fluorescence components are detected by the single photo-multiplier (multi-channel photo-multiplier), the excitation light is turned on and off at different time zones. Semiconductor lasers having a wavelength of 635 nm and constituting the excitation light source are turned on and off by turning on and off a signal for a power supply for driving the lasers. On the other hand, a beam of the YAG laser in the plurality-of-wavelength excitation system 22 is turned on and off by means of an acousto-optic modulator (AO modulator) not shown.

Figure 10:
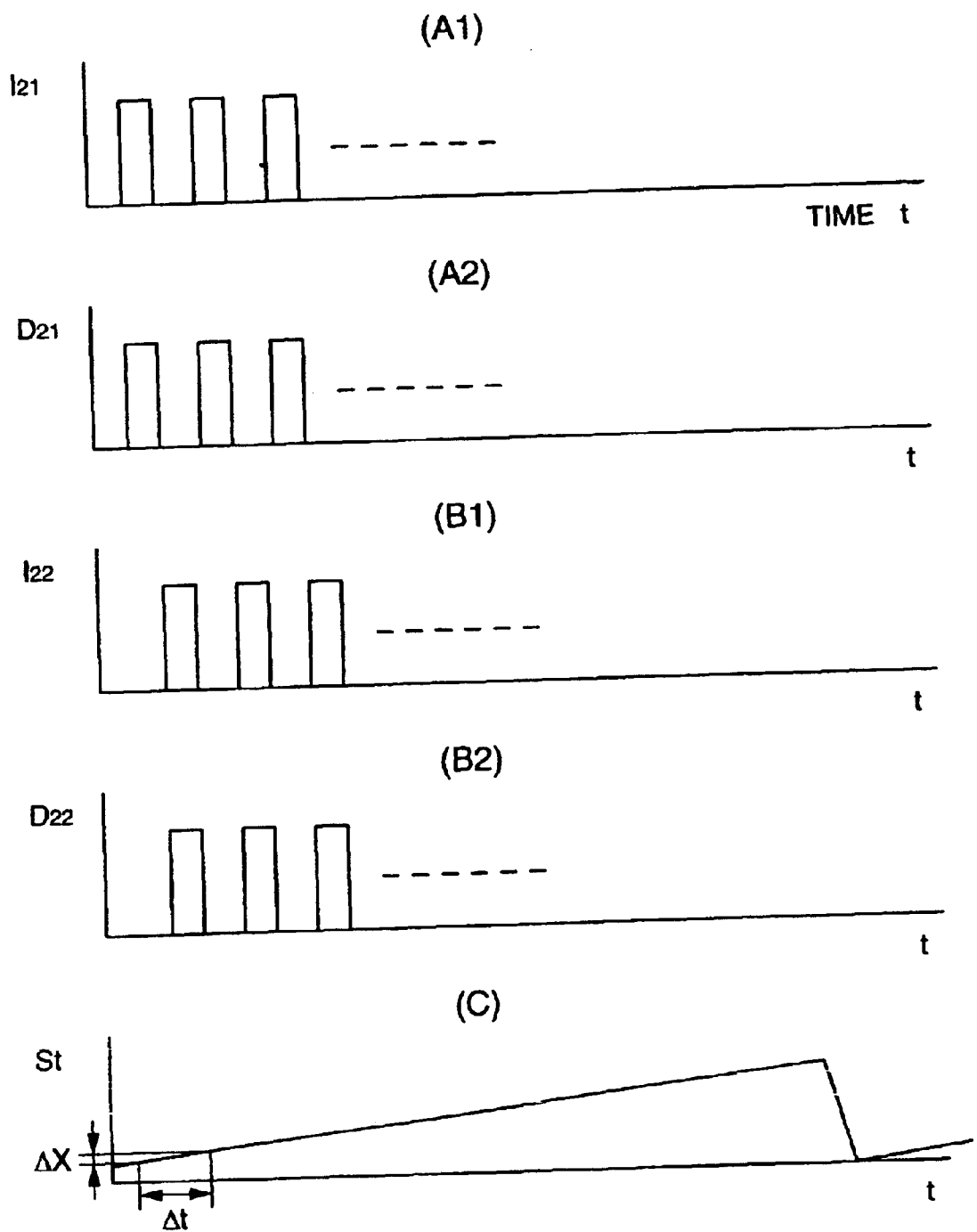
FIG. 10 is a graph showing a relation of temporal change in excitation light intensities and detection timings according to the present invention.

Intensities 121 and 122 of the excitation lights having the wavelengths of 635 nm and 532 nm, respectively, have time zones different from each other as shown by (A1) and (B1) of FIG. 10 and in which the excitation lights are turned on and off. The turning on time of the excitation lights is several tens μs to several hundreds μs. In almost all fluorescence materials, since a delay time in emission of fluorescence after excitation is several ns to several hundreds ns, fluorescence is emitted in almost concurrence with an irradiation time of the excitation light. Accordingly, respective fluorescence components are detected in synchronism with turning on and off of the excitation light as shown by (A2) and (B2) of FIG. 10. (C) of FIG. 10 shows a relation of a movement amount or positional information St of the stage for holding the sample in synchronism with turning on and off of the excitation light and detecting fluorescence at different positions and time. That is, movement is made by Δx during a time Δt for detecting fluorescence components at 64 spots in response to turning on and off of the two excitation lights. This movement distance can be made approximately equal to a diameter d of the spot to thereby detect fluorescence in a desired area by means of scanning and turning on and off.

Figure 8:
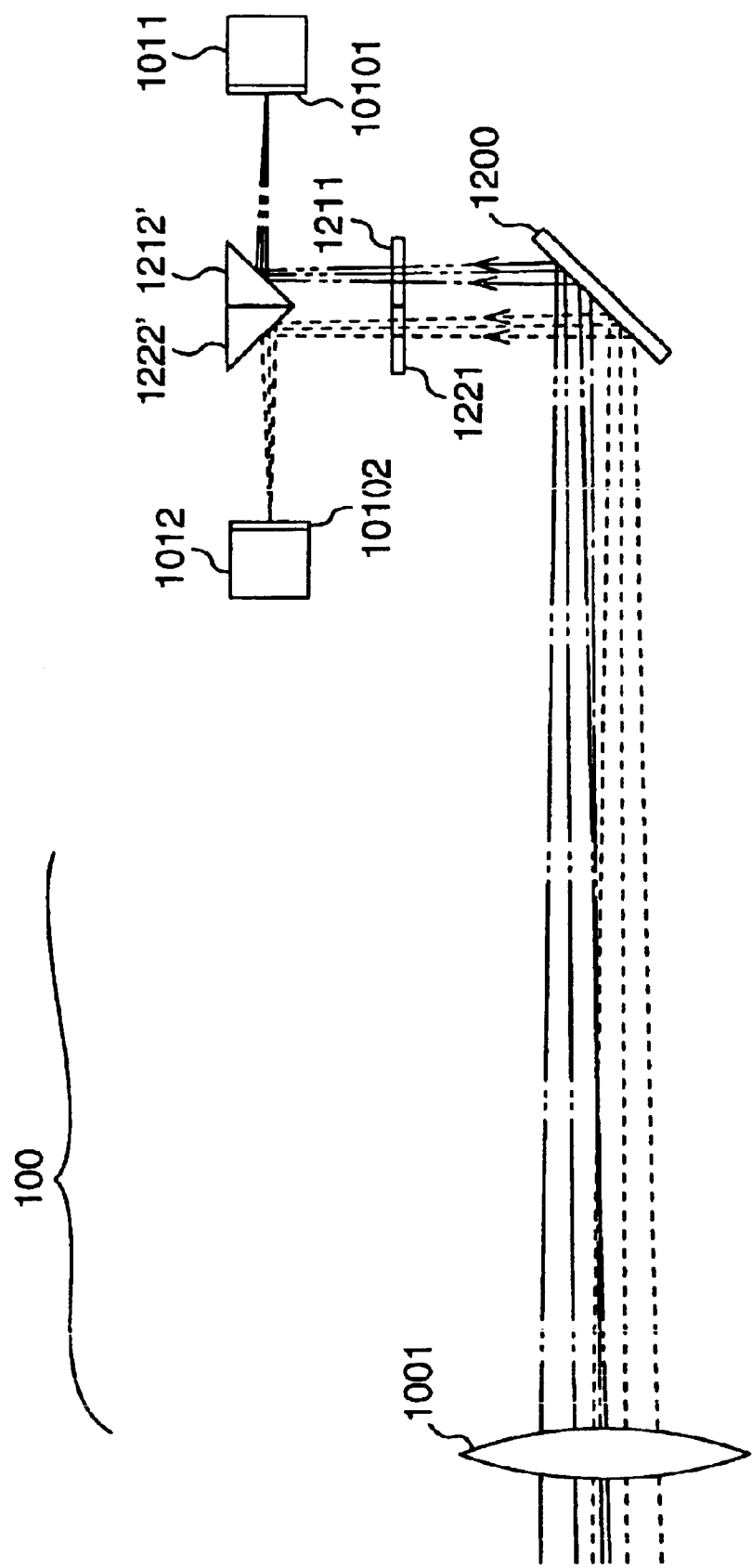
FIG. 8 is a diagram representing a relation of a plurality of fluorescence samples and the photo-multiplier according to the present invention.

FIG. 8 shows an embodiment according to the present invention in which irradiation with excitation lights having a plurality of wavelengths are made at the same time to detect fluorescence at the same time. In this case, DNA sample or fluorescence material sample is irradiated with two (or three or more) excitation lights concurrently at the same place thereof (a different place may be irradiated). When the same place is irradiated with the excitation lights having the plurality of wavelengths, positions and inclinations of the wavelength selection beam splitters 31 and 34 are previously adjusted. With such adjustment, fluorescence emitted by the excitation light having the wavelength of 635 nm, for example, can pass through the interference filter 1211 of FIG. 8 and fluorescence emitted by the excitation light having the wavelength of 532 nm can pass through the interference filter 1221 of FIG. 8. Consequently, the respective fluorescence components can be reflected by the mirrors 1212' and 1222' and enter different multi-channel photo-multipliers 1011 and 1012 to thereby detect the fluorescence components separately at the same time.

Figure 9:
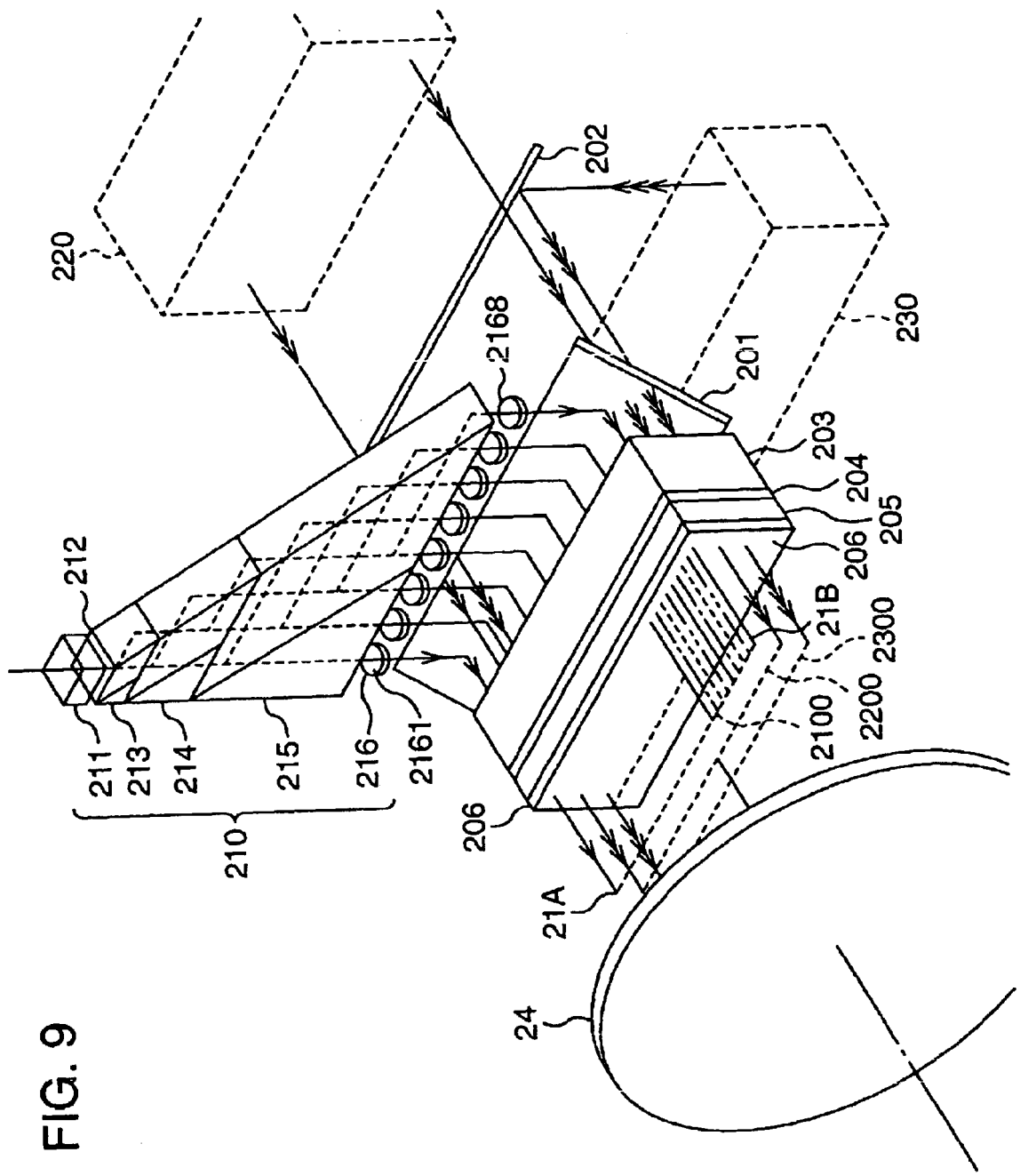
FIG. 9 is a perspective view showing a plurality-of-wavelength excitation optical system according to the present invention.

FIG. 9 is a diagram showing an embodiment according to the present invention in which three kinds of excitation lights are used by way of example. Numeral 210 denotes a multi-spot excitation light system using a semiconductor laser having a wavelength of 635 nm (λ11), 220 a multi-spot excitation light system using a wavelength of 590 to 600 nm (λ12), and 230 a multi-spot excitation light system using a laser having a wavelength of 532 nm (λ13). A method of converting lights emitted from the respective light sources into multi-spots will be described using the multi-spot excitation light system 210.

The beam emitted from the light source is shaped to have a desired beam diameter and spread angle by means of a beam shaping unit not show in drawings and is converted to have a desired polarization state by a polarizer 212. The polarized beam passes through beam splitters 213, 214 and 215. The beam splitters are each composed of an isosceles right triangle and a parallelogram with apical angles of 45 degrees having a hypotenuse stuck on a hypotenuse of the isosceles right angle and the stuck surface or side constitutes a beam splitting surface. Further, when the distance between the stuck side of the parallelogram and its opposite side of the beam splitter 213 is d, the corresponding distances of the beam splitters 214 and 215 are 2d and 4d, respectively. Consequently, the beam passing through the beam splitter 215 is increased to 8 beams and the space between the beams is equal to √2d. The 8 beams form multiple spots having the desired beam diameter on 21A to 21B lines 2100 by means of convex lenses array 2161 to 2168.

Numerals 220 and 230 of FIG. 9 also represent multi-spot excitation optical systems having such structure. A wavelength selection beam splitter 202 transmits excitation light having a wavelength λ12 and reflects excitation light having a wavelength λ13. A wavelength selection beam splitter 201 transmits excitation lights having wavelengths λ12 and λ13 and reflects excitation light having a wavelength λ11.

The multiple beams having 8 beams of the excitation lights having three wavelengths are increased to 32 beams equal to four times by means of beam splitters 203 and 205 made of, for example, calcite of birefringent material and wave plates 204 and 206 and form multiple spots by a desired beam system on straight lines 2200 and 2300 on surfaces 21A and 21B. The sample 5 is irradiated with the multiple spots of the three excitation lights formed on the straight lines 2100, 2200 and 2300 in this space at a desired spot diameter by means of the tubular lens 24 and the objective lens 3 described in FIG. 1.

Figure 11:
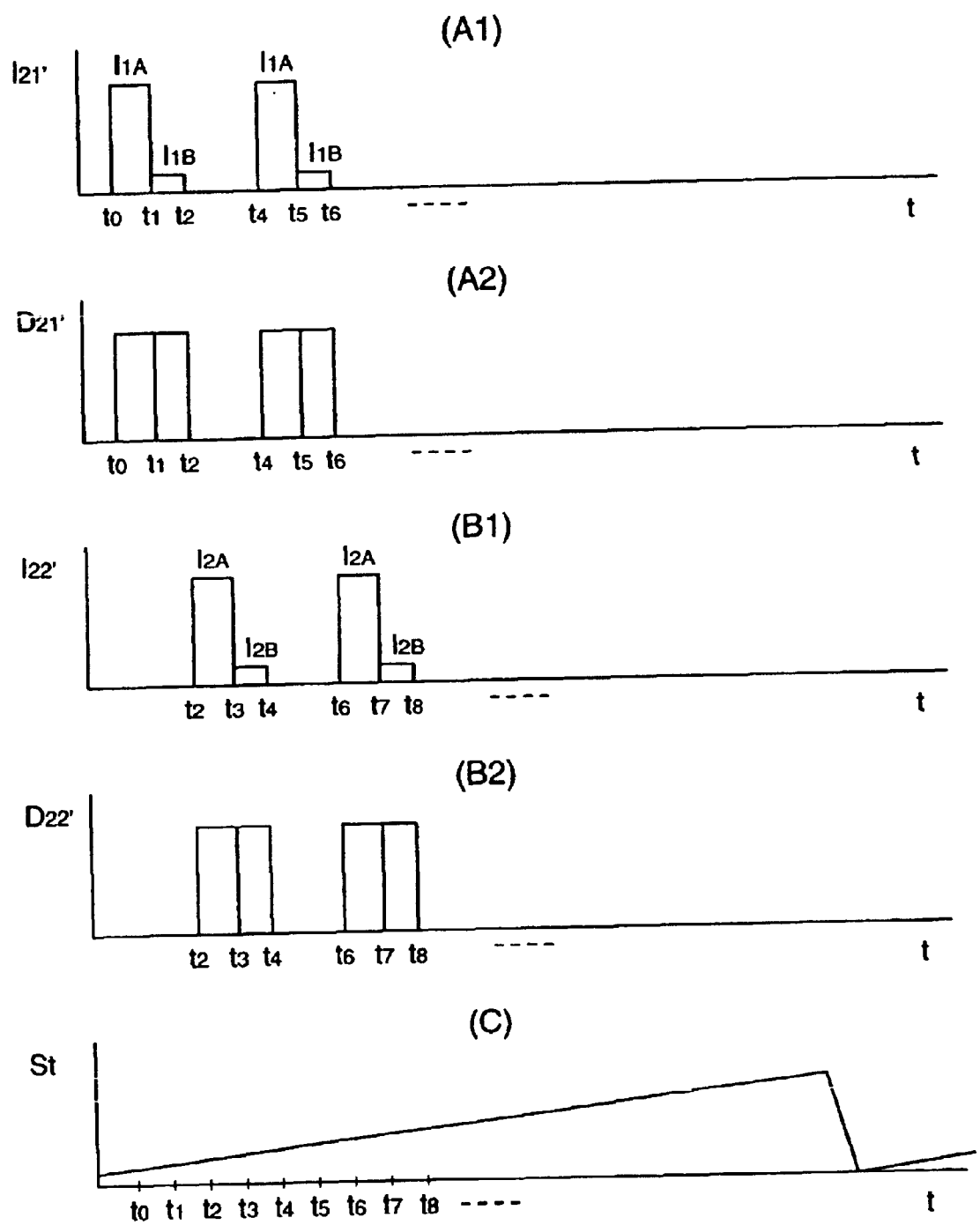
FIG. 11 is a graph showing a relation of temporal change in excitation light intensities and detection timings according to the present invention.

FIG. 11 shows an embodiment according to the present invention in which there are two excitation wavelengths. In order to set a dynamic range for detection of fluorescence largely, it is necessary to change the intensity of excitation light to detect fluorescence. That is, when fluorescence having the number of molecules of fluorescence per unit area to be detected equal to an extremely small value to a large value such as, for example, one molecule/$\mu m^2$ to 10 thousands molecules/$\mu m^2$ is to be detected, the detection resolution (detection range/noise level) of a high-sensitivity detector such as a photo-multiplier is exceeded. Accordingly, this problem is solved by the method shown in FIG. 11. (A1) and (B1) of FIG. 11 have the abscissa representing time and the ordinate representing the intensities on the sample of excitation lights having excitation wavelengths λ1 and λ2, respectively. In the embodiment, detection using the excitation lights λ1 and λ2 is made in the time series manner, while the following description can be similarly applied to the case where the detection is made at the same time. During time t0 to t2, excitation is made by the excitation light λ1 to detect fluorescence. During time t0 to t1, excitation is made by strong light I1A as the intensity I21' of excitation light and during time t1 to t2, excitation is made by weak light I1B as the intensity I21' of excitation light. As shown by (A2) and (B2) of FIG. 11, fluorescence is detected by the excitation light intensities I1A and I1B in the zones t0 to t1 and t1 to t2, respectively.

Similarly, during time t2 to t4, as shown by (B1) of FIG. 11, the excitation light intensity I22' for the excitation light of λ2 is set to I2A during time t2 to t3 and to I2B during time t3 to t4. As shown by (B2) of FIG. 11, respective fluorescence intensities are detected in respective time zones.

Figure 12:
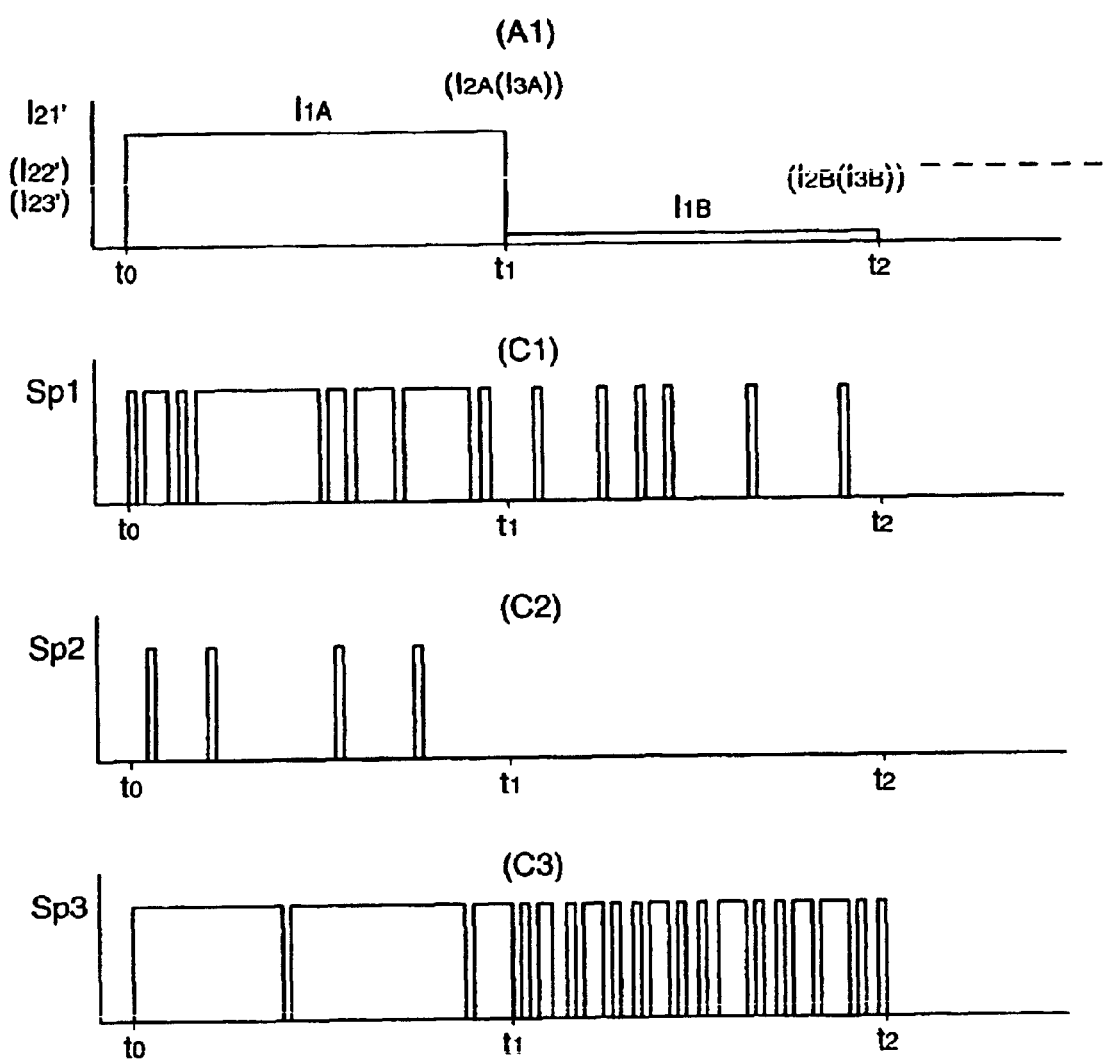
FIG. 12 is a graph showing a photon counting and detecting method according to the present invention.

FIG. 12 shows a detection method of a signal of a photo-multiplier which can be applied to the case where the number of fluorescence molecules is very small to the case where it is large. When the number of fluorescence molecules is small, a photon-counting method is applied. The photon-counting method is effective for the case where light is weakened and the number of photon pulses is about several counts to several hundreds or several thousands counts within a detection time. Conversely, when fluorescence is increased too much, photon-pulses are frequently detected within a time width of a pulse signal and the pulses cannot be counted exactly. In such case, as described with reference to FIG. 11, by reducing the fluorescence light intensity extraordinarily to irradiate fluorescence with it, overlap of photon-pulses can be reduced and fluorescence can be detected.

(A1) of FIG. 12 is similar to (A1) of FIG. 11 with the exception that the time axis of the abscissa is enlarged. In the embodiment, three kinds of fluorescence molecules are detected at the same time while scanning the sample and the excitation light relatively. That is, the sample is irradiated with two or three kinds of excitation lights at the same time as shown by (A1) of FIG. 12. Relative values of the respective excitation lights are I1A, I2A and (I3A) and I1B, I2B and (I1B) having extraordinarily weak intensity. Counts of photon-pulses of fluorescence obtained from three kinds of fluorescence materials L1, L2 and L3 are shown by (C1), (C2) and (C3) of FIG. 12. The fluorescence material L1 has approximately medium intensity of fluorescence, L2 weak intensity, and L3 very strong intensity.

There are two pulse-counting methods including a first method of counting a pulse having even a large pulse width as one pulse as shown in FIG. 12 and a second method of measuring a time that a pulse signal is high. In the first method, when the number of pulses is increased, a count is reduced conversely, so that the relation of the detection intensity and the pulse count is not a single-valued function and the count cannot be specified. On the contrary, in the second method, even if the number of pulses is increased, a count is not reduced and the relation of the detection intensity and the pulse count is a single-valued function, so that exact measurement can be made by correcting the count. The second method can make more exact counting, although when the width of pulses is small, it is difficult to make exact counting if the time constant of the counting circuit is not made very small.

In the embodiment of FIG. 12, since irradiation with strong excitation light and weak excitation light is made to count photons in respective cases, the counting can be made substantially without error even in the first method that the single-valued function is not obtained from the respective counts for the strong and weak excitation lights. That is, in the case of (C1) of FIG. 12, if a count obtained during time t0 to t1 is not largely changed from a count obtained during time t1 to t2, it is understood that the latter value is correct. Further, as shown by (C3) of FIG. 12, when a count obtained during time t0 to t1 is small and a count obtained during time t1 to t2 is large, it is understood that the latter value is correct. On the other hand, as shown by (C2) of FIG. 12, when a count obtained during time t1 to t2 is almost 0, it is understood that the count obtained during time t0 to t1 is correct.

Moreover, when a wider dynamic range is required, the intensity of the excitation light shown by (A1) of FIGS. 11 and 12 is set to three stages including a very strong excitation light, an approximately medium excitation light, and a very weak excitation light to thereby make it possible to attain detection in a wider dynamic range.

Figure 13:
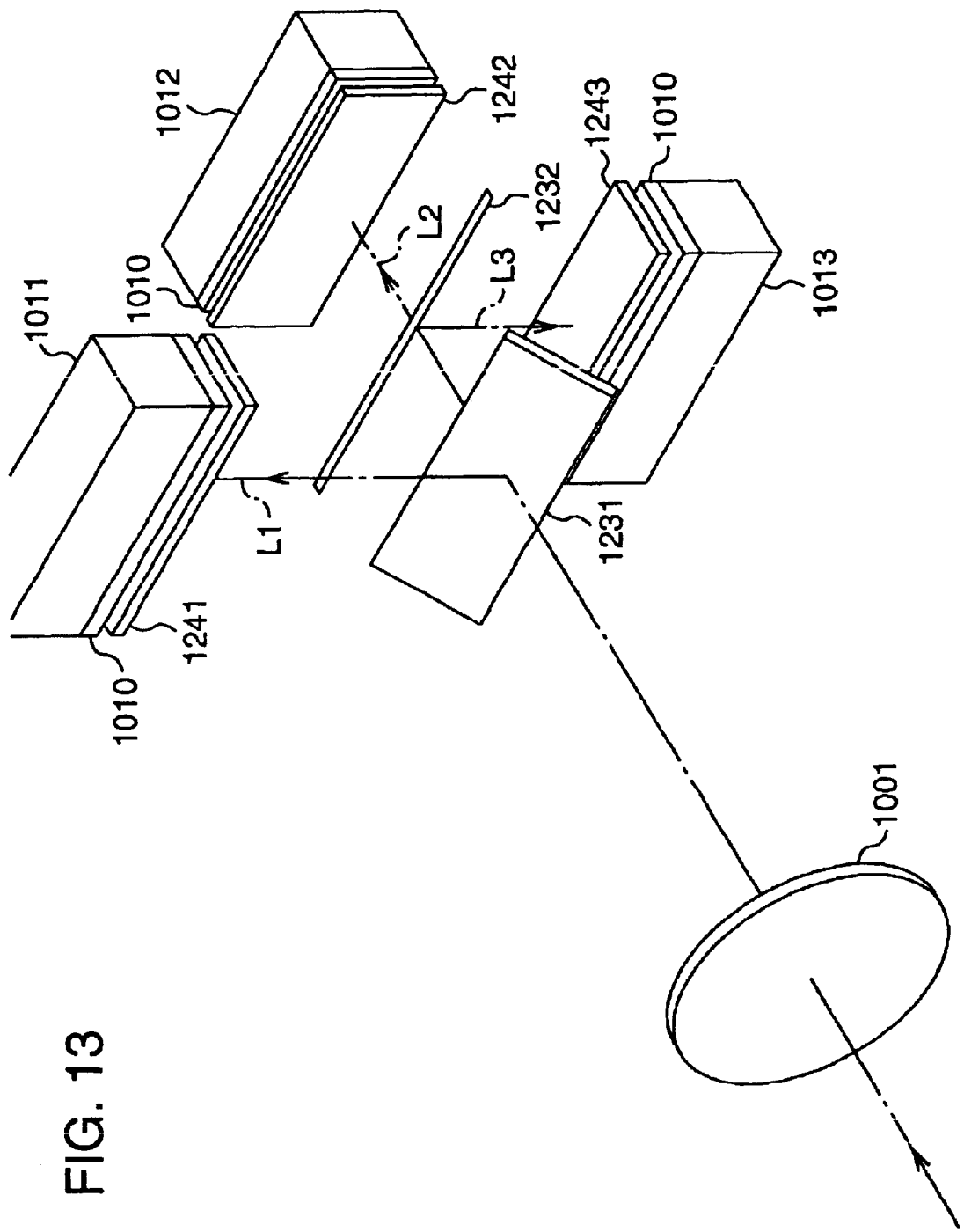
FIG. 13 is a perspective view showing a fluorescence detection unit according to the present invention.

FIG. 13 shows an embodiment according to the present invention in which only a fluorescence detection portion is shown. In the excitation light irradiation optical system, the wavelength selection beam splitters 201 and 202 are aligned so that three excitation lights 2100, 2200 and 2300 of FIG. 9 have the same optical path. The sample 5 shown in FIG. 1 is irradiated with three multi-spot excitation lights 2100', 2200' and 2300' at the same place so that fluorescence components L1, L2 and L3 obtained are detected as follows. The fluorescence component L1 is reflected by the wavelength selection beam splitters 32 and 34 of FIG. 1 and the fluorescence components L2 and L3 transmit the wavelength selection beam splitter 32, are reflected by the wavelength selection beam splitter 31 and transmit the wavelength selection beam splitter 34 to thereby be led to the fluorescence detection portion shown in FIG. 13. The fluorescence obtained from the multi-spot excitation light on the sample is focused on light receiving portion of the multi-channel photo-multipliers 1011, 1012 and 1013 as a multi-spot image by means of the objective lens 3 of FIG. 1 and the tubular lens 1001 of FIG. 13. The fluorescence components obtained from three fluorescent marks are separated by means of wavelength separation beam splitters 1231 and 1232 of FIG. 13. That is, the fluorescence component L1 obtained by the excitation light 2100' is reflected by the wavelength separation beam splitter 1231, passes through an interference filter 1241 which transmits only this fluorescence component and then passes through an opening of a multi-pinhole array 1010 to thereby be detected by the multi-channel photo-multiplier 1011. Similarly, the fluorescence components L2 and L3 pass through the wavelength selection beam splitter 1231. The fluorescence component L2 transmits the wavelength selection beam splitter 1232 and the fluorescence component L3 is reflected by the wavelength selection beam splitter 1232. Both the fluorescence components then transmit interference filters 1242 and 1243 and are detected by the multi-channel photo-multipliers 1012 and 1013, respectively.

In the embodiment shown in FIG. 13, three wavelengths are used as the excitation light, while two wavelengths may be used as the excitation light to detect three fluorescence materials. That is, a semiconductor laser having a wavelength of 635 nm and a YAGSHG laser having a wavelength of 532 nm may be used as excitation light sources to detect Cy5 (R), Cy3.5 (R) and Cy3 (R) as fluorescence materials. In this case, since peak values of respective fluorescence spectra are in the vicinity of 670, 570 and 600 nm, the wavelength selection beam splitter 1231 is set to reflect the wavelength of 650 nm or more and transmit the wavelength smaller than 650 nm. Further, the wavelength selection beam splitter 1232 is set to reflect the wavelength of 585 nm or more and transmit the wavelength smaller than 585 nm.

With the detection of fluorescence as described above, by relatively scanning the excitation light and the sample on a slide glass over a desired area of, for example, 20×40 mm of the slide glass once, concentration of a plurality of fluorescence materials can be detected as fluorescence intensities.

In the description of the embodiment, the multi-spot array is used as the excitation light by way of example, while even a single spot or excitation light in the form of elongate sheet extending in the direction perpendicular to the scanning direction may be used to attain high-speed detection similarly.

It will be further understood by those skilled in the art that the foregoing description has been made on embodiments of the invention and that various changes and modifications may be made in the invention without departing from the spirit of the invention and scope of the appended claims.

What is claimed is:

1. A DNA inspection method comprising irradiating a sample having a DNA piece added with a plurality of L kinds of fluorescence-marked materials combined to corresponding DNA with minute spot excitation lights having a plurality of M kinds of wavelengths in accordance with said fluorescence-marked materials, separately detecting fluorescence intensities obtained in accordance with said fluorescence-marked materials, and changing said spot excitation lights and a position on the sample irradiated with said spot excitation lights over a desired area relatively by the number of times smaller than the number L of kinds of the fluorescence-marked materials to inspect said DNA added with said plurality of L kinds of fluorescence-marked materials.

2. A DNA inspection method according to claim 1, wherein said relatively changing operation of said spot excitation lights and the position on the sample irradiated with said spot excitation lights over the desired area is made once.

3. A DNA inspection method according to claim 1, wherein said plurality of M kinds of minute spot excitation lights are a plurality of N minute multi-spot excitation lights.

4. A DNA inspection method according to claim 1, wherein different positions on the sample from one another are irradiated with said plurality of M kinds of multi-spot excitation lights.

5. A DNA inspection method according to claim 1, wherein irradiation with said plurality of M kinds of multi-spot excitation lights is made at the same time and fluorescence obtained by said plurality of kinds of minute spot excitation lights in accordance with said fluorescence-marked materials is detected by a plurality of K weak-light detection elements in accordance with respective excitation lights, the fluorescence intensities obtained in accordance with the fluorescence-marked materials being detected separately.

6. A DNA inspection method according to claim 1, wherein irradiation with said plurality of M kinds of minute spot excitation lights is made in time series manner in accordance with wavelengths of said excitation lights and fluorescence obtained by said plurality of kinds of minute spot excitation lights in accordance with said fluorescence-marked materials is detected by a common weak-light detection element to respective excitation lights, the fluorescence intensities obtained in accordance with the fluorescence-marked materials being detected separately.

7. A DNA inspection method according to claim 6, wherein substantially the same position is irradiated with said plurality of M kinds of minute spot excitation lights.

8. A DNA inspection method according to claim 1, wherein said plurality of M kinds of minute spot excitation lights are turned on and off in different time zone within a time that a relative position of said spot excitation lights and said sample to be irradiated is changed by substantially one pixel.

9. A DNA inspection method according to claim 1, wherein said plurality of M kinds of minute spot excitation lights are changed stepwise at respective excitation light intensity levels within a time that a relative position of said spot excitation lights and said sample to be irradiated is changed by substantially one pixel to detect the fluorescence intensity at each step, so that detection is made over a wide dynamic range at a high speed.

10. A DNA inspection method according to claim 1, wherein said separate detection of fluorescence intensities is made by a photon-counting method.

11. A DNA inspection apparatus comprising one to a plurality of light sources for emitting lights having a plurality of M kinds of wavelengths different from one another, a plurality-of-wavelength excitation optical system for irradiating a DNA sample added with a plurality of L kinds of fluorescence-marked materials with lights having said plurality of wavelengths from said light sources as minute spot excitation lights, a wavelength separation fluorescence detection system for separately detecting fluorescence intensities obtained by the respective excitation lights in accordance with said fluorescence-marked materials, a driving stage for changing a relative position of said minute spot excitation lights and said DNA sample over a desired area, plurality-of-fluorescent-mark simultaneous processing means for constructing fluorescent image information of a plurality of L kinds of fluorescence-marked DNA on said sample from fluorescence detection information and fluorescence detection position information obtained by scanning said desired area once in response to change of said relative position, means for collectively processing information obtained by said plurality-of-fluorescent-mark simultaneous processing means and storing inspection result, and output means for outputting the result stored in said storing means in a desired output format.

12. A DNA inspection apparatus according to claim 11, wherein said plurality-of-wavelength excitation optical system produces, as said minute spot excitation lights, N multiple spots having said respective different wavelengths.

13. A DNA inspection apparatus according to claim 11, wherein said light source or said plurality-of-wavelength excitation optical system includes means for turning on and off said excitation lights having respective wavelengths alternately in time series manner.

14. A DNA inspection apparatus according to claim 11, wherein said light source or said plurality-of-wavelength excitation optical system includes means for changing intensities of said excitation lights having respective wavelengths in accordance with detected fluorescence intensities.

15. A DNA inspection apparatus according to claim 11, wherein said wavelength separation fluorescence detection system makes detection by counting photons.

16. A fluorescence detection method comprising irradiating a sample containing a plurality of L kinds of fluorescent materials with minute spot excitation lights having a plurality of M kinds of wavelengths in accordance with said fluorescent materials, separately detecting fluorescence intensities obtained in accordance with said respective fluorescent materials, and changing said spot excitation lights and a position on the sample irradiated with said spot excitation lights over a desired area relatively by the number of times smaller than the kinds L of said fluorescent materials to detect fluorescence on said sample added with said plurality of L kinds of fluorescent materials.

17. A fluorescence detection method according to claim 16, wherein said relatively changing operation of said spot excitation lights and the position on the sample irradiated with said spot excitation lights over the desired area is made once.

\* \* \* \* \*